United States Patent [19]

Nagase

[11] 4,362,546
[45] * Dec. 7, 1982

[54] TETRAHYDROPHTHALAMIDE DERIVATIVES, HERBICIDAL COMPOSITIONS AND USE

[75] Inventor: Hiroshi Nagase, Kawanishi, Japan

[73] Assignee: Takeda Chemical Industries, Ltd., Osaka, Japan

[*] Notice: The portion of the term of this patent subsequent to May 4, 1982, has been disclaimed.

[21] Appl. No.: 153,098

[22] Filed: May 27, 1980

[30] Foreign Application Priority Data

May 28, 1979 [JP] Japan ................... 54-66565

[51] Int. Cl.³ ............... A01N 37/22; C07C 103/737; C07D 295/18
[52] U.S. Cl. .................... 71/88; 71/92; 71/94; 71/95; 71/105; 71/118; 544/165; 544/391; 546/226; 564/155; 564/158; 260/239 A; 260/239 E; 260/239 BF; 260/465 D; 548/538
[58] Field of Search .............. 544/165, 391; 260/239 E, 239 A, 239 BF, 326.41, 465 D, 239 AR; 546/226; 71/92, 94, 95, 88, 105, 118; 564/155, 158

[56] References Cited

PUBLICATIONS

Wakabayashi et al., Chem. Abstracts, vol. 92, (1980), No. 163729h, Abstract of Ger. Offen. 2,921,002, Nov. 29, 1979.

Nagase, Chem. Abstracts, vol. 91, (1979), No. 157464l, Abstract of Ger. Offen. 2,851,379, May 31, 1979.
Matsui et al., Japanese Publication No. 48-96722, (1973).
Klingman et al., Weed Science: Principles and Practices, John Wiley & Sons, p. 100.

Primary Examiner—Robert W. Ramsuer
Attorney, Agent, or Firm—Burgess, Ryan and Wayne

[57] ABSTRACT

Tetrahydrophthalamide derivatives of the general formula:

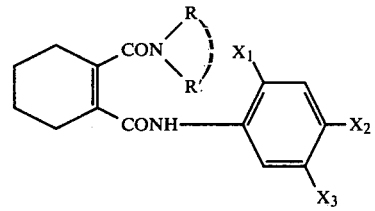

wherein $X_1$ is hydrogen or halogen; $X_2$ is halogen, alkoxy or substituted benzyloxy; $X_3$ is hydrogen, alkoxy or alkenyloxy; R and R' are the same or different alkyl, cycloalkyl, alkenyl or phenyl, each of which may be optionally substituted, or may jointly, together with nitrogen atom adjacent to R and R', form aliphatic heterocyclic ring containing one or two nitrogens or nitrogen and oxygen, which have a herbicidal activity against a broad spectrum of monocotyledonous and dicotyledonous weeds.

23 Claims, No Drawings

TETRAHYDROPHTHALAMIDE DERIVATIVES, HERBICIDAL COMPOSITIONS AND USE

The present invention relates to tetrahydrophthalamide derivatives of the general formula (I):

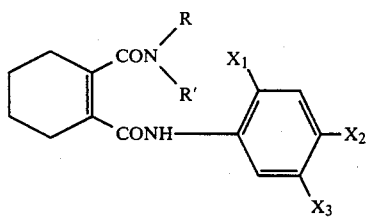

wherein $X_1$ is hydrogen or halogen; $X_2$ is halogen, alkoxy or substituted benzyloxy; $X_3$ is hydrogen, alkoxy or alkenyloxy; R and R' are the same or different alkyl, cycloalkyl, alkenyl or phenyl, each of which may be optionally substituted, or may jointly, together with the nitrogen atom adjacent to R and R', form an aliphatic heterocyclic ring containing one or two nitrogens or nitrogen and oxygen, to a method for producing them, and to a herbicidal composition containing any of the aforesaid tetrahydrophthalamide derivatives (I).

The present inventor, after comprehensive and extensive research on amide compounds having a herbicidal effect, found that the above-mentioned compounds (I) possess strong weed-killing activity, and has completed the present invention.

Thus, the present inventor has completed the present invention, on the basis of the findings that the above-mentioned novel compounds display excellent herbicidal activity against a broad spectrum of paddy-field weeds such as barnyard grass *Echinochloa oryzicola* Vasing., umbrella plant *Cyperus difformis* L., monochoria *Monochoria vaginalis* PRESL., false pimpernel *Lindernia procumbens* Philcox, toothcup *Rotala indica* KOEHNE etc., spikerush *Eleocharis acidularis* Roem. et Schult., etc. and tilled land weeds such as crabgrass *Digitaria adscendens* HENR., pig weeds *Amaranthus retroflexus* L., lamb's quarters *Chenopodium album* L., inutade *Polygonum Blumei* Meisn. and common purslane *Portulaca oleracea* L., etc., and that in view of the high selectivity of compounds (I) as applied in pre-emergence treatment to crop plants, particularly to leguminous plants, these compounds (I) are able to selectively control the aforementioned weeds without causing any substantial injury to soybean and other crop plants.

Thus, the present invention relates to:
(1) Tetrahydrophthalamide compounds (I),
(2) A process for producing tetrahydrophthalamide compounds (I), which comprises reacting a compound of the general formula (II):

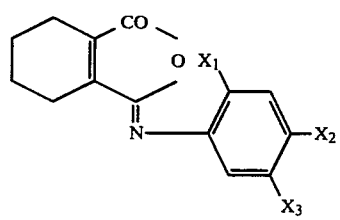

wherein $X_1$ is hydrogen or halogen; $X_2$ is halogen, alkoxy or substituted benzyloxy; $X_3$ is hydrogen, alkoxy or alkenyloxy, with a compound of the general formula (IV):

wherein R and R' are the same or different alkyl, cycloalkyl, alkenyl or phenyl, each of which may be optionally substituted, or may jointly, together with nitrogen atom adjacent to R and R', form aliphatic heterocyclic ring containing one or two nitrogens or nitrogen and oxygen, or reacting a compound of the general formula (III):

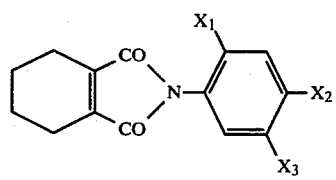

wherein the symbols are as defined above, with a compound of the general formula (IV):

wherein the symbols are as defined above, and (3) A herbicidal composition containing as an active ingredient one or more species of tetrahydrophthalamide derivatives (I) and a suitable carrier therefor.

Referring to the general formulas mentioned above, the halogen atoms designated by $X_1$ or $X_2$, which are employable, include fluorine, chlorine and bromine, and fluorine or chlorine is preferable as $X_1$, and chlorine or bromine is preferable as $X_2$, particularly preferred being the combination of fluorine by $X_1$ and chlorine by $X_2$; employable as the alkoxy groups represented by $X_2$ or $X_3$ are, for example, straight-chain or branched-chain alkyloxy groups such as methoxy, ethoxy, propoxy, isopropoxy, butoxy, isobutoxy, sec-butoxy, t-butoxy, pentyloxy, isopentyloxy and hexyloxy, and alkyloxy groups having 1 to 3 carbon atoms, among others, are preferred; examples of the substituents on substituted benzyloxy designated by $X_2$ include halogen atoms such as chlorine, bromine and fluorine, lower alkyls (preferably, those having 1 to 3 carbon atoms), such as methyl and ethyl, and halomethyl such as trifluoromethyl, etc., and the preferred substituents are halogen atoms, and the halogen-substituted benzyloxy groups which are employable include 4-chlorobenzyloxy, 4-bromobenzyloxy, 4-fluorobenzyloxy, 3,4-dichlorobenzyloxy, etc.; employable as the alkenyloxy designated by $X_3$ are, for example, alkenyloxy groups having 2 to 6 carbon atoms, preferably 3 carbon atoms, such as allyloxy, methallyloxy, pentenyloxy, butenyloxy and hexenyloxy, and the alkenyloxy groups may be substituted by a lower alkyl group (preferably, having 1 to 3 carbon atoms) such as methyl and ethyl and a halogen atom such as chlorine and bromine.

Referring again to the general formulas mentioned above, the alkyls designated by R or R', which are employable, include straight-chain or branched-chain alkyl groups such as methyl, ethyl, propyl, isopropyl, butyl, isobutyl, sec-butyl, t-butyl, pentyl, isopentyl, hexyl, heptyl, octyl, nonyl, decyl, lauryl and stearyl, and the alkyl groups having 1 to 10 carbon atoms, particularly 1 to 4 carbon atoms, among others, are preferred; examples of the substituent on such alkyl may include hydroxyl, cyano, halogen atoms such as chlorine and bromine, straight-chain or branched-chain alkoxy groups having 1 to 3 carbon atoms such as methoxy, ethoxy, isopropoxy and n-propoxy and groups represented by the general formula,

wherein Y is hydrogen, halogen or lower alkyl; m is an integer of 1, 2 or 3. In the formula (V), as the preferred examples of the halogen are mentioned chlorine and bromine, and the lower alkyl which is desirable includes alkyl groups having 1 to 3 carbon atoms. Such groups which are often usable are typified by unsubstituted phenyl.

Among the alkyl groups having the substituent group, particularly desirable one is a straight-chain alkyl having 1 to 4 carbon atoms. And, such alkyl may have two or more of the same or different substituents.

Examples of the cycloalkyl which may be employable include cycloalkyl groups having 3 to 8, preferably 3 to 6 carbon atoms, such as cyclopropyl, cyclobutyl, cyclopentyl and cyclohexyl. Such cycloalkyls may be substituted by a lower alkyl having 1 to 4 carbon atoms such as methyl and ethyl, halogen atoms such as chlorine and bromine, etc. Employable as the alkenyl are, for example, alkenyl groups having 2 to 8, preferably 3 carbon atoms, such as allyl, methallyl, pentenyl, butenyl and hexenyl, and such alkenyl groups may be substituted by a lower alkyl such as methyl and ethyl, phenyl and the like.

The phenyl group designated by R or R' may be substituted by the same alkyl or alkoxy group as described above. Such substituted phenyls which are employable include phenyls substituted by straight-chain or branched-chain alkyl of 1 to 4 carbon atom (e.g. o-tolyl, m-tolyl, p-tolyl, p-ethylphenyl, p-propylphenyl, p-isopropylphenyl, p-butylphenyl and p-isobutylphenyl), and phenyls substituted by straight-chain or branched-chain alkyloxy of 1 to 4 carbon atoms (e.g. p-methoxyphenyl, o-ethoxyphenyl, p-propoxyphenyl, p-isopropoxyphenyl and p-butyloxyphenyl). Where R and R' may jointly, together with the nitrogen atom adjacent to R and R', form an aliphatic heterocyclic ring containing one or two nitrogens or nitrogen and oxygen, there may be mentioned, as such ring, aziridine, azetidine, piperidine, pyrrolidine, hexahydroazepine, piperazine, N-methylpiperazine, morpholine, 2,6-dimethylmorpholine, 2-pyrroline, 3-pyrroline, 2-pipecoline and 3-pipecoline rings.

Among the aforesaid compounds [I], preferred ones may be classified as follows;
 (i) compounds wherein $X_1$ is hydrogen, $X_2$ is chlorine, fluorine or bromine, $X_3$ is hydrogen, and R and R' are as defined hereinbefore,
 (ii) compounds wherein $X_1$ is hydrogen, $X_2$ is chlorine or bromine, $X_3$ is alkoxy having 1 to 3 carbon atoms or allyloxy, and R and R' are as defined hereinbefore,
 (iii) compounds wherein $X_1$ is chlorine, $X_2$ is chlorine, $X_3$ is alkoxy having 1 to 3 carbon atoms or allyloxy, and R and R' are as defined hereinbefore, or
 (iv) compounds wherein $X_1$ is fluorine, $X_2$ is chlorine or bromine, $X_3$ is hydrogen, and R and R' are as defined hereinbefore.

The most preferred compounds among these classes are those of class (iv), particularly important, among others, being the compounds in which $X_1$ is fluorine, $X_2$ is chlorine, $X_3$ is hydrogen, and either one of R and R' is methyl or ethyl and the other is n-butyl, benzyl, phenyl which may be optionally substituted by methyl or methoxy; or R and R' may jointly form, together with nitrogen atom adjacent to R and R', piperidino, pyrrolidino, morpholino, 2,6-dimethylmorpholino or N-methylmorpholino.

The compounds of the class (iv) are characterized in that they have marked weed-killing activity against tilled land weeds.

Such compounds (I) may be produced, for example, by reacting a compound (II) with a compound (IV). The compounds (IV) may be used in the free form or in the form of salts that do not adversely affect the reaction. Examples of the salts of the compound (IV) which may be useful include salts with hydrogen halides such as hydrogen chloride and hydrogen bromide, inorganic or organic acids such as sulfuric acid, nitric acid, oxalic acid and acetic acid, etc.

The reaction is conducted by reacting 1 mole of the compound (II) with normally 0.8 to several moles, preferably 0.9 to 1.2 moles, of the compound (IV). The reaction is desirably carried out in an inert solvent inclusive of hydrocarbons such as benzene, toluene, xylene, hexane and cyclohexane, halogenated hydrocarbons such as dichloromethane, chloroform, carbon tetrachloride and chlorobenzene, ethers such as diethylether, dioxane and tetrahydrofuran, acetonitrile, acetone, methyl ethyl ketone, ethyl acetate and nitrobenzene. The reaction temperature is normally in the range of 5° to 60° C., preferably in the range of 10° to 40° C. The reaction time is normally within the range of 5 minutes to 10 hours, preferably within the range of 10 minutes to 3 hours.

In the reaction, a catalyst may be added so as to promote the reaction. Examples of such catalysts which are normally used include Bronsted acids such as hydrogen chloride, Lewis acids such as aluminium chloride, boron trifluoride, etc.

The compounds (I) thus obtained may be isolated and purified by the procedures conventional per se, such as concentration, concentration under reduced pressure, solvent extraction, phasic transfer, crystallization, recrystallization and chromatographic separation.

The compounds (I) may also be produced by reacting a compound (III) with a compound (IV). The compounds (IV) may be used in the free state or in the form of salts as mentioned above. The reaction can be carried out under the conditions similar to those for the reaction between the compounds (II) and (IV). Consequently, amounts of raw materials, solvents, temperature, time duration, isolation methods and others may be appropriately selected and employed in the same manner as those described above.

Furthermore, a tetrahydrophthalamide compound (I) may also be produced, for example, by the methods of:

Subjecting tetrahydrophthalamic acid and amines (IV) to direct dehydration;

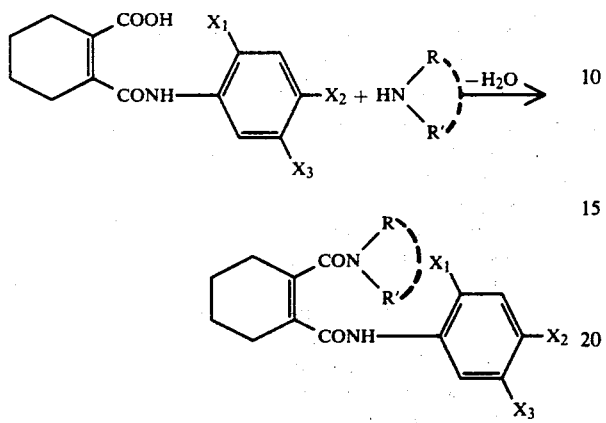

wherein the symbols are as defined above,

Reacting tetrahydrophthalamic acid ester with amines (IV);

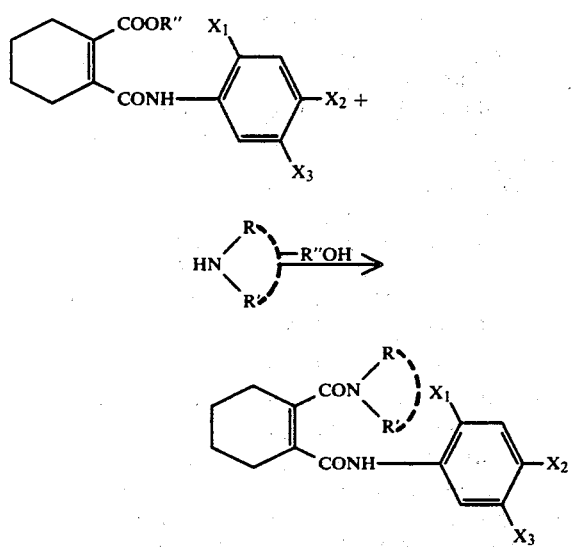

wherein the symbols are as defined; R" is a hydrocarbon residue such as methyl, ethyl, propyl, benzyl and phenyl, or Reacting tetrahydrophthalamic acids with electrophilic reagents designated by R'Y or RY in the presence of a base:

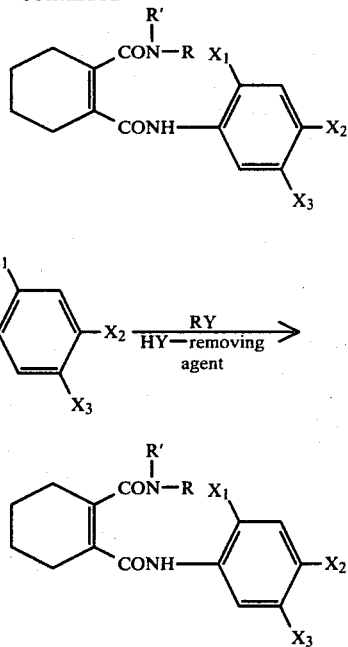

wherein the symbols are as defined above; Y is an active radical, e.g. a halogen atom and allene sulfonyloxy, as being normally used to allow the R or R' in RY or R'Y to react on the nitrogen atom as an electrophilic reagent.

These reactions can be carried out under the conditions conventional per se.

The starting compound (II) has been described in Japanese Patent Application Laid-Open (KOKAI) No. 23926/1978 and can be synthesized in accordance therewith, while the starting compound (III) is synthesized, for example, by the method as described in "Chemical Reviews," 1957, 641, or the methods similar thereto.

The compounds (I) produced by the above-mentioned methods show strong herbicidal activity in soil treatment or foliar application, and kill a broad spectrum of monocotyledonous and dicotyledonous weeds.

On the other hand, the present compounds (I), when applied by soil treatment in advance of germination to crops such as corn, soybeans, cotton and transplanted paddy rice, can efficiently kill a wide range of weeds without causing any substantial damage to such crops. In addition, the present compounds are low in toxicity to mammals and fishes, and offer the advantage of being applied without health hazard.

In using the compound (I) of the present invention as a herbicide, one or more kinds of the compounds (I), depending upon the application purposes, are dissolved or dispersed in an appropriate liquid carrier (e.g., solvent), or mixed with, or absorbed in, a suitable solid carrier (e.g., a diluent or extender), followed by further adding, if required, an emulsifying agent, suspending agent, spreader, penetrant, wetting agent, thickening agent, stabilizers, etc., to employ in the preparation forms such as oil preparations, wettable powders, dusts, granules, tablets, spraying agents, ointments, etc. These preparations can be prepared by the procedures conventional per se.

While the concentration of the active component compound or compounds in such a herbicidal composition varies with the intended application, it is suitable to employ about 10 to 90 weight percent in the case of emulsifiable concentrates or wettable powders, for instance; about 0.1 to 10 weight percent in the case of oil solutions and dusts; and about 1 to 20 weight percent in the case of granules. It should, however, be understood that deviations from the above-indicated range are permissible depending upon the intended application. In using the emulsifiable concentrates and wettable powders, these preparations are advantageously applied as diluted with a diluent such as water to a suitable concentration (e.g. 100 to 100000-fold).

As examples of the aforesaid liquid carrier (solvent) for use in the preparation of the present herbicidal compositions, there may be mentioned water, alcohols (e.g. methanol, ethanol, ethylene glycol, etc.), ketones (e.g. acetone, methyl ethyl ketone, etc.), ethers (e.g. dioxane, tetrahydrofuran, cellosolve, etc.), aliphatic hydrocarbons (e.g. gasoline, kerosene, fuel oil, machine oil, etc.), aromatic hydrocarbons (e.g. benzene, toluene, xylene, solvent naphtha, methylnaphthalene, etc.), halogenated hydrocarbons (e.g. chloroform, carbon tetrachloride, etc.), acid amides (e.g. dimethylformamide, etc.), esters (e.g. ethyl acetate, butyl acetate, fatty acid glycerol esters, etc.), nitriles (e.g. acetonitrile, etc.) and other solvents. These solvents are used alone or as a mixture. The solid carrier (diluent or volume-builder) may for example be any or a mixture of such carriers as vegetable powders (e.g. soybean meal, tobacco leaf powder, wheat flour, saw dust, etc.), mineral powders (e.g. kaolin, bentonite, acid clay and other clays; talc powder, agalmatolite and other varieties of talc; diatomaceous earth, mica powder and other forms of silica), alumina, calcium phosphate, flowers of sulfur, activated carbon and so on. These solid carriers may be employed alone or as an optional mixture.

As bases for said ointment there may be employed, among others, polyethylene glycol, pectin, polyhydric alcohol esters of higher fatty acids (e.g. glyceryl monostearate), cellulose derivatives (e.g. methyl-cellulose), sodium alginate, bentonite, higher alcohols (e.g. glycerol and other polyhydric alcohols), vaseline, petrolatum album, liquid paraffin, lard, vegetable oils, lanolin, dehydrated lanolin, hydrogenated oil, waxes, resins and so forth. These ointment bases may be employed alone or as a mixture, with or without the addition of surfactants or other additives.

As the surfactants used as emulsifiers, extenders, penetrants, dispersing agents, etc., there may be mentioned soaps, polyoxyalkylaryl esters (e.g. Nonal ®, Takemoto Yushi K.K. Japan), alkylsulfates (e.g. Emal 10 ®, Emal 40 ®, Kao Atlas K.K. Japan), alkylsulfonates (e.g. Neogen ®, Neogen T ®, Daiichi Kogyo Seiyaku K.K. Japan, Neopelex ®, Kao Atlas K.K. Japan), polyethylene glycol ethers (e.g. Nonipol 85 ®, Nonipol 100 ®, Nonipol 160 ®, Sanyo Kasei K.K. Japan), polyhydric alcohol esters (e.g. Tween 20 ®, Tween 80 ®, Kao Atlas K.K. Japan) and so on.

For use as a herbicide, the active compound (I) is applied in the amount of about 1 to about 50 g, preferably about 2 to about 40 g, per are of a paddy-rice field or about 1 to about 50 g, preferably about 2 to about 40 g, per are of a dry field. Preferably the compounds (I) are used as a pre-emergence herbicide. The compounds (I) are low in toxicity to mammalian animals and fishes, thus being suited for use in agricultural applications. In herbicidal compositions containing the compound (I) there may be further incorporated other herbicides, plant growth regulators, fungicides (e.g. organochlorine fungicides, organosulfur fungicides, antibiotics, etc.), insecticides (e.g. organophosphorus insecticides, natural insecticides, etc.), miticides, nematocides, synergists, attractants, repellents, pigments, fertilizers and so on.

EXAMPLE 1

N,N-dimethyl-N'-(4-chlorophenyl)-3,4,5,6-tetrahydrophthalamide (Compound No. 1)

In 100 ml of carbon tetrachloride is dissolved 3.0 g of N-(4-chlorophenyl)-3,4,5,6-tetrahydroisophthalimide. To the solution is added 1.5 g of a 40% aqueous dimethylamine solution under stirring at room temperature, followed by further stirring for 15 minutes. The reaction mixture is concentrated under reduced pressure. The resultant oily substance is dissolved in 50 ml of ether. The ether solution is dried with sodium sulfate and the ether layer is concentrated to dryness under reduced pressure. 50 ml of n-hexane is added to the resultant oily substance, and the solution is allowed to stand for a while, from which crystals are separated out. The resultant crystals are recovered by filtration and washed with a small amount of n-hexane to yield 2.7 g of the subject compound.

Melting point: 125° C.

EXAMPLE 2

N-methyl-N-butyl-N'-(4-chlorophenyl)-3,4,5,6-tetrahydrophthalamide (Compound No. 3)

In 100 ml of acetone is dissolved 3.0 g of N-(4-chlorophenyl)-3,4,5,6-tetrahydroisophthalimide. To the solution is added 1.2 g of N-methyl-butylamine under stirring at room temperature, followed by adding further 0.025 ml of a 5% ether solution of boron trifluoride thereto. The solution is stirred for 1 hour, and then shaken with 100 ml of ice water.

The resultant crystals are recovered by filtration, and washed with water and with a small amount of hexane. Recrystallization from n-hexane results in the subject compound. Yield: 2.3 g melting point: 102° C.–103° C.

EXAMPLE 3

N,N-dimethyl-N'-(3-isopropoxy-4-bromophenyl)-3,4,5,6-tetrahydrophthalamide (Compound No. 45)

In 50 ml of carbon tetrachloride is dissolved 2.5 g of N-(3-isopropoxy-4-bromophenyl)-3,4,5,6-tetrahydroisophthalimide. To the solution is added 0.9 g of a 40% aqueous dimethylamine solution under stirring at room temperature. The solution is further stirred for 20 minutes, followed by concentration to dryness under reduced pressure. To the concentrate is added n-hexane. The resultant crystals are recovered by filtration and washed with a small amount of n-hexane, to yield 2.3 g of the subject compound.

Melting point: 137° C.–138° C.

EXAMPLE 4

N,N-dimethyl-N'-(3-methoxy-4-chlorophenyl)-3,4,5,6-tetrahydrophthalamide (Compound No. 35)

In 100 ml of carbon tetrachloride is dissolved 2.5 g of N-(3-methoxy-4-chlorophenyl)-3,4,5,6-tetrahydroisophthalimide. To the solution is added 1.0 g of a 40% aqueous dimethylamine solution under stirring at room temperature. The solution is further stirred for 20 minutes, followed by recovering the resultant crystals by filtration and washing with a small amount of n-hexane, to yield 2.2 g of the subject compound.

Melting point: 144° C.–145° C.

EXAMPLE 5

N,N-dimethyl-N'-(3-allyloxy-4-chlorophenyl)-3,4,5,6-tetrahydrophthalamide (Compound No. 39)

In 30 ml of toluene is dissolved 3.0 g of N-(3-allyloxy-4-chlorophenyl)-3,4,5,6-tetrahydroisophthalimide. To the solution is added 1.2 g of a 40% aqueous dimethylamine solution, followed by stirring at room temperature for 20 minutes. After adding 50 ml of n-hexane thereto, the resultant crystals are recovered by filtration and washed with a small amount of ether, to yield 2.5 g of the subject compound.

Melting point: 129° C.–131° C.

EXAMPLE 6

N,N-diethyl-N'-(3-ethoxy-4-chlorophenyl)-3,4,5,6-tetrahydrophthalamide (Compound No. 37)

To 50 ml of acetone is added 3.0 g of N-(3-ethoxy-4-chlorophenyl)-3,4,5,6-tetrahydroisophthalimide and a solution of 0.8 g of diethylamine in 5 ml of acetone is dropwise added to the solution over the period of about 3 minutes under stirring at room temperature. The solution is stirred at room temperature for a further 4 hours and the solvent is distilled off under reduced pressure for concentration, and recrystallization of the resultant residue from n-hexane yields 2.2 g of the subject compound.

Melting point: 98° C.–100° C.

EXAMPLE 7

N,N-diethyleneoxy-N'-(3-methoxy-4-chlorophenyl)-3,4,5,6-tetrahydrophthalamide (Compound No. 36)

In 100 ml of acetonitrile is dissolved 3.0 g of N-(3-methoxy-4-chlorophenyl)-3,4,5,6-tetrahydroisophthalimide. To the solution is added 1.0 g of morpholine under stirring at room temperature, followed by further stirring for 30 minutes. The resultant crystals are recovered by filtration and washed with a small amount of acetonitrile, to yield 3.8 g of the subject compound.

Melting point: 157° C.

EXAMPLE 8

N,N-dimethyl-N'-(2-fluoro-4-bromophenyl)-3,4,5,6-tetrahydrophthalamide (Compound No. 97)

In 20 ml of toluene is dissolved 2.5 g of N-(2-fluoro-4-bromophenyl)-3,4,5,6-tetrahydroisophthalimide. To the solution is added 1.0 g of a 40% aqueous dimethylamine solution under stirring at room temperature. The solution is further stirred for 15 minutes and then washed with water. The toluene layer is dried with sodium sulfate and is concentrated to dryness under reduced pressure. By adding n-hexane, the resultant oily substance is allowed to crystallize. The crystals are recovered by filtration and washed with a small amount of n-hexane, to yield 2,0 g of the subject compound.

Melting point: 83° C.–85° C.

EXAMPLE 9

N,N-dimethyl-N'-(4-chlorophenyl)-3,4,5,6-tetrahydrophthalamide (Compound No. 1)

In 100 ml of acetonitrile is dissolved 3.0 g of N-(4-chlorophenyl)-3,4,5,6-tetrahydrophthalimide. To the solution is added 1.5 g of a 40% aqueous dimethylamine solution under stirring at room temperature, followed by further stirring for 30 minutes. The solution is concentrated to dryness under reduced pressure, the resulting oily substance is dissolved in 50 ml of ether and the solution is dried with sodium sulfate. The ether layer is concentrated to dryness under reduced pressure and the resultant oily substance is allowed to crystallize by adding 50 ml of n-hexane thereto. The resultant crystals are recovered by filtration and washed with a small amount of n-hexane, whereby to yield 2.5 g of the subject compound.

Melting point: 125° C.

EXAMPLE 10

N,N-diethyl-N'-(2-fluoro-4-chlorophenyl)-3,4,5,6-tetrahydrophthalamide (Compound No. 70)

In 50 ml of acetone is dissolved 2.8 g of N-(2-fluoro-4-chlorophenyl)-3,4,5,6-tetrahydrophthalimide. To the solution is added 0.8 g of diethylamine under stirring at room temperature. After further stirring for 30 minutes, the solution is concentrated to dryness under reduced pressure, followed by adding 50 ml of n-hexane to cool. The resultant crystals are recovered by filtration and recrystallized from n-hexane, to yield 2.0 g of the subject compound. Melting point: 105° C.–106° C.

The reaction is conducted by means of the same or similar procedures as described in above-mentioned Examples 1 through 10 to synthesize different species of the compounds (I). The compounds (I) synthesized are tabulated in Table I.

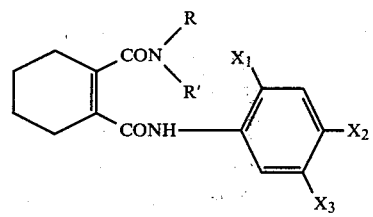

TABLE I

| Comp. No. | R | R' | $X_1$ | $X_2$ | $X_3$ | m.p., °C. |
|---|---|---|---|---|---|---|
| 1 | CH₃ | CH₃ | H | Cl | H | 125 |
| 2 | C₂H₅ | C₂H₅ | H | Cl | H | 105–106 |
| 3 | CH₃ | n-C₄H₉ | H | Cl | H | 102–103 |
| 4 | CH₃ | ⟨C₆H₅⟩—CH₂ | H | Cl | H | 132–133 |
| 5 | CH₃ | ⟨C₆H₅⟩— | H | Cl | H | 174–176 |

TABLE I-continued

| Comp. No. | R | R' | $X_1$ | $X_2$ | $X_3$ | m.p., °C. |
|---|---|---|---|---|---|---|
| 6 | | $-(CH_2)_4-$ | H | Cl | H | 142 |
| 7 | | $-(CH_2)_5-$ | H | Cl | H | 152 |
| 8 | | $-(CH_2)_2O(CH_2)_2-$ | H | Cl | H | 153 |
| 9 | $CH_3$ | $CH_3$ | H | Br | H | 143-144 |
| 10 | $C_2H_5$ | $C_2H_5$ | H | Br | H | 100-101 |
| 11 | $n-C_3H_7$ | $n-C_3H_7$ | H | Br | H | 133-134 |
| 12 | $CH_2=CH-CH_2-$ | $CH_2=CH-CH_2-$ | H | Br | H | 109-110 |
| 13 | | $-(CH_2)_4-$ | H | Br | H | 156-157 |
| 14 | | $-(CH_2)_5-$ | H | Br | H | 153-154 |
| 15 | | $-(CH_2)_2-O-(CH_2)_2-$ | H | Br | H | 148-149 |
| 16 | $CH_3$ | $CH_3$ | H | F | H | 105-106 |
| 17 | $C_2H_5$ | $C_2H_5$ | H | F | H | 94-95 |
| 18 | $n-C_3H_7$ | $n-C_3H_7$ | H | F | H | 101-102 |
| 19 | $CH_2=CH-CH_2-$ | $CH_2=CH-CH_2-$ | H | F | H | 85-86 |
| 20 | | $-(CH_2)_4-$ | H | F | H | 143-144 |
| 21 | | $-(CH_2)_5-$ | H | F | H | 175-176 |
| 22 | $CH_3$ | $CH_3$ | H | $CH_3O-$ | H | 130-131 |
| 23 | | $-(CH_2)_4-$ | H | $CH_3O-$ | H | 145-146 |
| 24 | | $-(CH_2)_5-$ | H | $CH_3O-$ | H | 126-127 |
| 25 | | $-(CH_2)_2-O-(CH_2)_2-$ | H | $CH_3O-$ | H | 124-125 |
| 26 | $CH_3$ | $CH_3$ | H | 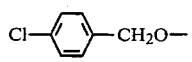 | H | 133-135 |
| 27 | $C_2H_5$ | $C_2H_5$ | H | 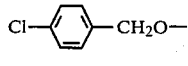 | H | 113-114 |
| 28 | $CH_3$ | $n-C_4H_9$ | H | 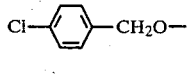 | H | 120 |
| 29 | $CH_3$ | $C_6H_5-CH_2-$ | H | 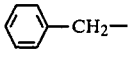 | H | 112-113 |
| 30 | | $-(CH_2)_4-$ | H | 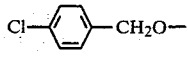 | H | 117-118 |
| 31 | | $-(CH_2)_5-$ | H | 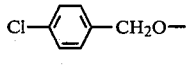 | H | 150-151 |
| 32 | | $-(CH_2)_6-$ | H | 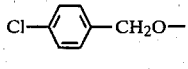 | H | 135-136 |
| 33 | | $-(CH_2)_2-O-(CH_2)_2-$ | H | 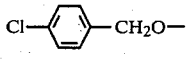 | H | 141-142 |
| 34 | | $-(CH_2)_2-N(CH_3)-(CH_2)_2-$ | H | 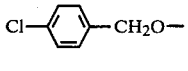 | H | 128-129 |
| 35 | $CH_3$ | $CH_3$ | H | Cl | $CH_3O-$ | 144-145 |
| 36 | | $-(CH_2)_2-O-(CH_2)_2-$ | H | Cl | $CH_3O-$ | 157 |
| 37 | $C_2H_5-$ | $C_2H_5-$ | H | Cl | $C_2H_5O-$ | 98-100 |
| 38 | $CH_3$ | $CH_3$ | H | Cl | $i-C_3H_7O-$ | 140-141 |
| 39 | $CH_3$ | $CH_3$ | H | Cl | $CH_2=CH-CH_2O-$ | 129-132 |
| 40 | | $-(CH_2)_2-O-(CH_2)_2-$ | H | Cl | $CH_2=CH-CH_2O-$ | 148-149 |
| 41 | $CH_3$ | | H | Br | $CH_3O-$ | 160-162 |
| 42 | | $-(CH_2)_5-$ | H | Br | $CH_3O-$ | 166 |
| 43 | | $-(CH_2)_2-O-(CH_2)_2-$ | H | Br | $CH_3O-$ | 151-153 |
| 44 | | $-CH_2CH=CH-CH_2-$ | H | Br | $CH_3O-$ | 170 |
| 45 | $CH_3$ | $CH_3$ | H | Br | $i-C_3H_7O-$ | 137-138 |
| 46 | $C_2H_5$ | $C_2H_5$ | H | Br | $i-C_3H_7O-$ | 96-97 |
| 47 | $n-C_3H_7$ | $n-C_3H_7$ | H | Br | $i-C_3H_7O-$ | 93 |
| 48 | $CH_2=CH-CH_2-$ | $CH_2=CH-CH_2-$ | H | Br | $i-C_3H_7O-$ | 101-102 |
| 49 | $n-C_4H_9$ | $n-C_4H_9$ | H | Br | $i-C_3H_7O-$ | 76-78 |
| 50 | | $-(CH_2)_5-$ | H | Br | $i-C_3H_7O-$ | 126-127 |
| 51 | | $-(CH_2)_2-O-(CH_2)_2-$ | H | Br | $i-C_3H_7O-$ | 145-146 |
| 52 | $CH_3$ | $CH_3$ | H | Br | $CH_2=CH-CH_2O-$ | 122-124 |
| 53 | $CH_2=CH-CH_2-$ | $CH_2=CH-CH_2-$ | H | Br | $CH_2=CH-CH_2O-$ | 92-94 |
| 54 | | $-(CH_2)_6-$ | H | Br | $CH_2=CH-CH_2O-$ | 154-155 |
| 55 | | $-CH_2CH=CH-CH_2-$ | H | Br | $CH_2=CH-CH_2O-$ | 131-132 |
| 56 | | $-(CH_2)_2O(CH_2)_2-$ | H | Br | $CH_2=CH-CH_2O-$ | 131-133 |

TABLE I-continued

| Comp. No. | R | R' | $X_1$ | $X_2$ | $X_3$ | m.p., °C |
|---|---|---|---|---|---|---|
| 57 | \-(CH_2)_2-N(CH_3)-(CH_2)_2- | | H | Br | $CH_2=CH-CH_2O-$ | 139–141 |
| 58 | $CH_3$ | $CH_3$ | Cl | Cl | $i\text{-}C_3H_7O-$ | 124–125 |
| 59 | $C_2H_5$ | $C_2H_5$ | Cl | Cl | $i\text{-}C_3H_7O-$ | 114–116 |
| 60 | $CH_3$ | $n\text{-}C_4H_9$ | Cl | Cl | $i\text{-}C_3H_7O-$ | 92–93 |
| 61 | $CH_2=CH-CH_2$ | $CH_2=CH-CH_2$ | Cl | Cl | $i\text{-}C_3H_7O-$ | 95–97 |
| 62 | $-(CH_2)_5-$ | | Cl | Cl | $i\text{-}C_3H_7O-$ | 123–125 |
| 63 | $CH_3$ | $CH_3$ | Cl | Cl | $CH_2=CH-CH_2O-$ | 123–124 |
| 64 | $C_2H_5$ | $C_2H_5$ | Cl | Cl | $CH_2=CH-CH_2O-$ | 69–71 |
| 65 | $-(CH_2)_4-$ | | Cl | Cl | $CH_2=CH-CH_2O-$ | 146–148 |
| 66 | $-(CH_2)_5-\cdot\tfrac{1}{2}H_2O$ | | Cl | Cl | $CH_2=CH-CH_2O-$ | 99–100 |
| 67 | $-(CH_2)_2O(CH_2)_2-$ | | Cl | Cl | $CH_2=CH-CH_2O-$ | 95–96 |
| 68 | $-(CH_2)_2-N(CH_3)-(CH_2)_2-$ | | Cl | Cl | $CH_2=CH-CH_2O-$ | 92–93 |
| 69 | $CH_3$ | $CH_3$ | F | Cl | H | 98 |
| 70 | $C_2H_5$ | $C_2H_5$ | F | Cl | H | 105–106 |
| 71 | $n\text{-}C_3H_7$ | $n\text{-}C_3H_7$ | F | Cl | H | 101–103 |
| 72 | $n\text{-}C_4H_9$ | $n\text{-}C_4H_9$ | F | Cl | H | 63–64 |
| 73 | $i\text{-}C_4H_9$ | $i\text{-}C_4H_9$ | F | Cl | H | 75–76 |
| 74 | $n\text{-}C_6H_{13}$ | $n\text{-}C_6H_{13}$ | F | Cl | H | 56 |
| 75 | $CH_3$ | $n\text{-}C_4H_9$ | F | Cl | H | 96 |
| 76 | $C_2H_5$ | $n\text{-}C_4H_9$ | F | Cl | H | 105–106 |
| 77 | $CH_2=CH-CH_2-$ | $CH_2=CH-CH_2-$ | F | Cl | H | 74–75 |
| 78 | $NC-CH_2CH_2-$ | $NC-CH_2CH_2-$ | F | Cl | H | 144–145 |
| 79 | $CH_3CH(OH)-CH_2-$ | $CH_3CH(OH)-CH_2-$ | F | Cl | H | 66 |
| 80 | $CH_3$ | $C_6H_5-CH_2-$ | F | Cl | H | 93–94 |
| 81 | $C_6H_5-CH_2-$ | $C_6H_5-CH_2-$ | F | Cl | H | 122–123 |
| 82 | $-(CH_2)_4-$ | | F | Cl | H | 97–99 |
| 83 | $-(CH_2)_5-$ | | F | Cl | H | 107–108 |
| 84 | $-(CH_2)_2-O-(CH_2)_2-$ | | F | Cl | H | 117–118 |
| 85 | $-CH_2CH(CH_3)-O-CH(CH_3)CH_2-$ | | F | Cl | H | 139 |
| 86 | $-(CH_2)_2-N(CH_3)-(CH_2)_2-$ | | F | Cl | H | 119–121 |
| 87 | $CH_3$ | phenyl | F | Cl | H | 117–119 |
| 88 | $C_2H_5$ | phenyl | F | Cl | H | 102–103 |
| 89 | $n\text{-}C_3H_7$ | phenyl | F | Cl | H | 85–86 |
| 90 | $n\text{-}C_4H_9$ | phenyl | F | Cl | H | 92–93 |
| 91 | $CH_3$ | 2-methylphenyl | F | Cl | H | 119–121 |
| 92 | $CH_3$ | 3-methylphenyl | F | Cl | H | 110–111 |

TABLE I-continued

| Comp. No. | R | R' | $X_1$ | $X_2$ | $X_3$ | m.p., °C. |
|---|---|---|---|---|---|---|
| 93 | $C_2H_5$ | 2-CH$_3$-C$_6$H$_4$- | F | Cl | H | 119–120 |
| 94 | $C_2H_5$ | 3-CH$_3$-C$_6$H$_4$- | F | Cl | H | 104–105 |
| 95 | $C_2H_5$ | 4-CH$_3$-C$_6$H$_4$- | F | Cl | H | 112–113 |
| 96 | $CH_3$ | 4-CH$_3$O-C$_6$H$_4$- | F | Cl | H | 99–100 |
| 97 | $CH_3$ | $CH_3$ | F | Br | H | 83–85 |
| 98 | $C_2H_5$ | $C_2H_5$ | F | Br | H | 89–91 |
| 99 | n-$C_4H_9$ | n-$C_4H_9$ | F | Br | H | 60–62 |
| 100 | $CH_2=CH-CH_2-$ | $CH_2=CH-CH_2-$ | F | Br | H | 69–71 |
| 101 | $CH_3$ | $C_6H_5$- | F | Br | H | 141–142 |
| 102 | —(CH$_2$)$_5$— | | F | Br | H | 125–127 |
| 103 | —(CH$_2$)$_6$— | | F | Br | H | 115–117 |
| 104 | —(CH$_2$)$_2$—O—(CH$_2$)$_2$— | | F | Br | H | 108–110 |
| 105 | $CH_2=CH-CH_2-$ | 2-$C_2H_5$-C$_6$H$_4$- | F | Cl | H | 118–119 |
| 106 | $CH_3$ | $C_6H_5$- | F | Cl | H | 129–130 |

EXAMPLE 11

A wettable powder which comprises 50% by weight of N,N-dimethyl-N'-(2-fluoro-4-chlorophenyl)-3,4,5,6-tetrahydrophthalamide, 5% by weight of polyethylene glycol ether (Nonypol 85 ®) and 45% by weight of white carbon being mixed and crushed.

EXAMPLE 12

A granule which comprises kneading with water a mixture composed of 10% by weight of N,N-dimethyl-N'-(4-chlorophenyl)-3,4,5,6-tetrahydrophthalamide, 5% by weight of sodium lignin sulfonate and 85% by weight of bentonite, and granulating the mixture.

EXAMPLE 13

An emulsifiable concentrate which contains 20% by weight of N-methyl-N-butyl-N'-(2-fluoro-4-bromophenyl)-3,4,5,6-tetrahydrophthalamide, 75% by weight of xylene and 5% by weight of polyethylene glycol ether (Nonypol 85 ®).

EXAMPLE 14

A plastic pot of 900 cm$^2$ (30×30×10 cm) is filled with tilled land soil, and seeds of crabgrass, pig weeds, lamb's quarters, inutade (Polygonum), common purslane, maize, soybean and cotton are planted and covered 0.5 cm deep with soil. Then, using a spray gun, the surface of the soil was evenly sprayed with a dilution of the emulsifiable concentrate containing the compound (I). The emulsifiable concentrate was diluted with water amounting to 10 l per are to provide 2.5 g, 5 g or 10 g active component per are. After three weeks, the effects and injuries to the plants were investigated. The herbicidal effects are expressed according to the following index system.

| Index | Effect | % Inhibition (weed-killing) |
|---|---|---|
| 0 | No | 0% |
| 1 | Slight | 0.1–50% |
| 2 | Low | 50.1–70% |
| 3 | Moderate | 70.1–87.5% |
| 4 | High | 87.6–99.9% |
| 5 | very high | 100% |

The extent of injuries to plants is expressed with the following index system.

| Index | Degree of injury | % Injury |
|---|---|---|
| 0 | None | 0% |
| 1 | Slight | 0.1–12.5% |
| 2 | Low | 12.6–30.0% |
| 3 | Moderate | 30.1–50.0% |
| 4 | High | 50.1–99.9% |
| 5 | Very high | 100% |

The results are shown in Table II

TABLE II

| Comp. No. | Application rate, g/are | Crab-grass | Pig weed | Lamb's quarters | Poly-gonum | Common purs-lane | Maize | Soy-bean | Cot-ton |
|---|---|---|---|---|---|---|---|---|---|
| 1 | 2.5 | 4 | 5 | 5 | 4 | 5 | 1 | 0 | 1 |
|   | 5 | 4 | 5 | 5 | 5 | 5 | 1 | 0 | 1 |
| 2 | 10 | 4 | 5 | 4 | 3 | 5 | 0 | 0 | 0 |
| 3 | 5 | 4 | 5 | 5 | 3 | 5 | 2 | 0 | 1 |
| 4 | 5 | 4 | 4 | 3 | 2 | 5 | 0 | 0 | 0 |
|   | 10 | 4 | 5 | 3 | 4 | 5 | 0 | 0 | 1 |
| 5 | 5 | 4 | 4 | 3 | 3 | 5 | 0 | 0 | 0 |
|   | 10 | 4 | 5 | 5 | 4 | 5 | 3 | 1 | 1 |
| 6 | 5 | 4 | 5 | 5 | 5 | 5 | 1 | 0 | 1 |
|   | 10 | 5 | 5 | 5 | 5 | 5 | 3 | 0 | 2 |
| 7 | 2.5 | 4 | 4 | 3 | 4 | 5 | 0 | 0 | 0 |
|   | 5 | 4 | 4 | 5 | 4 | 5 | 1 | 0 | 0 |
| 8 | 2.5 | 4 | 5 | 4 | 3 | 5 | 2 | 0 | 1 |
|   | 5 | 5 | 5 | 4 | 5 | 5 | 2 | 0 | 1 |
| 9 | 5 | 4 | 4 | 4 | 5 | 5 | 0 | 0 | 0 |
|   | 10 | 4 | 5 | 4 | 5 | 5 | 1 | 0 | 0 |
| 10 | 10 | 3 | 4 | 5 | 4 | 5 | 0 | 0 | 0 |
| 12 | 10 | 4 | 5 | 4 | 4 | 5 | 1 | 1 | 0 |
| 13 | 10 | 4 | 5 | 5 | 4 | 5 | 0 | 0 | 0 |
| 14 | 5 | 4 | 3 | 3 | 4 | 5 | 0 | 0 | 0 |
|    | 10 | 4 | 5 | 3 | 4 | 5 | 0 | 0 | 0 |
| 15 | 5 | 4 | 4 | 3 | 4 | 5 | 0 | 0 | 0 |
|    | 10 | 4 | 5 | 3 | 4 | 5 | 1 | 0 | 0 |
| 16 | 10 | 4 | 3 | 4 | 4 | 5 | 1 | 0 | 0 |
| 17 | 10 | 4 | 2 | 3 | 4 | 5 | 0 | 1 | 0 |
| 18 | 10 | 3 | 2 | 4 | 4 | 5 | 1 | 1 | 0 |
| 19 | 10 | 4 | 3 | 3 | 4 | 5 | 1 | 2 | 0 |
| 20 | 10 | 4 | 4 | 3 | 4 | 5 | 0 | 0 | 0 |
| 21 | 10 | 4 | 3 | 3 | 4 | 5 | 1 | 0 | 0 |
| 23 | 10 | 3 | 2 | 2 | 4 | 5 | 0 | 0 | 0 |
| 35 | 5 | 1 | 5 | 4 | 5 | 5 | 0 | 0 | 0 |
| 37 | 5 | 1 | 5 | 4 | 4 | 5 | 0 | 0 | 0 |
| 38 | 2.5 | 1 | 5 | 5 | 5 | 5 | 0 | 0 | 0 |
|    | 5 | 1 | 5 | 5 | 5 | 5 | 0 | 0 | 0 |
| 39 | 5 | 3 | 5 | 5 | 5 | 5 | 0 | 0 | 1 |
|    | 10 | 4 | 5 | 5 | 5 | 5 | 0 | 0 | 1 |
| 40 | 10 | 1 | 4 | 4 | 4 | 5 | 0 | 0 | 0 |
| 41 | 10 | 3 | 4 | 4 | 4 | 5 | 0 | 0 | 0 |
| 45 | 5 | 3 | 4 | 5 | 5 | 5 | 0 | 0 | 1 |
|    | 10 | 3 | 5 | 5 | 5 | 5 | 0 | 0 | 1 |
| 48 | 10 | 3 | 5 | 5 | 5 | 5 | 1 | 0 | 0 |
| 50 | 5 | 3 | 5 | 4 | 4 | 5 | 0 | 0 | 0 |
|    | 10 | 3 | 5 | 4 | 4 | 5 | 0 | 0 | 0 |
| 58 | 2.5 | 2 | 5 | 5 | 3 | 5 | 0 | 0 | 0 |
|    | 5 | 3 | 5 | 5 | 3 | 5 | 0 | 0 | 0 |
| 61 | 2.5 | 1 | 3 | 5 | 3 | 5 | 0 | 0 | 0 |
|    | 5 | 2 | 4 | 5 | 5 | 5 | 0 | 0 | 0 |
| 62 | 2.5 | 1 | 5 | 4 | 2 | 5 | 0 | 0 | 0 |
|    | 5 | 2 | 5 | 5 | 3 | 5 | 0 | 0 | 0 |
| 63 | 10 | 2 | 4 | 5 | 4 | 5 | 0 | 0 | 0 |
| 67 | 10 | 3 | 4 | 5 | 4 | 5 | 0 | 0 | 0 |
| 69 | 2.5 | 5 | 5 | 5 | 5 | 5 | 1 | 0 | 0 |
| 70 | 5 | 4 | 4 | 4 | 3 | 5 | 0 | 0 | 0 |
| 71 | 2.5 | 4 | 4 | 4 | 3 | 5 | 0 | 0 | 0 |
|    | 5 | 4 | 5 | 5 | 4 | 5 | 1 | 0 | 1 |
| 72 | 5 | 4 | 4 | 4 | 3 | 5 | 0 | 0 | 0 |
| 73 | 10 | 4 | 2 | 3 | 3 | 5 | 0 | 0 | 0 |
| 74 | 5 | 4 | 4 | 4 | 4 | 5 | 0 | 0 | 0 |
| 75 | 2.5 | 4 | 5 | 5 | 4 | 5 | 0 | 0 | 0 |
|    | 5 | 5 | 5 | 5 | 5 | 5 | 1 | 0 | 0 |
| 76 | 2.5 | 5 | 5 | 5 | 5 | 5 | 1 | 0 | 1 |
| 77 | 5 | 4 | 5 | 5 | 5 | 5 | 1 | 0 | 1 |
| 79 | 5 | 5 | 5 | 4 | 2 | 5 | 0 | 0 | 1 |
| 80 | 2.5 | 5 | 5 | 5 | 5 | 5 | 1 | 0 | 0 |
| 81 | 5 | 5 | 5 | 5 | 5 | 5 | 1 | 0 | 0 |
| 82 | 2.5 | 5 | 5 | 5 | 4 | 5 | 1 | 0 | 1 |
| 83 | 2.5 | 5 | 5 | 5 | 4 | 5 | 1 | 0 | 1 |
| 84 | 2.5 | 5 | 5 | 5 | 4 | 5 | 1 | 0 | 0 |
| 85 | 2.5 | 5 | 5 | 5 | 5 | 5 | 2 | 0 | 0 |
| 86 | 2.5 | 5 | 5 | 5 | 5 | 5 | 1 | 0 | 0 |
| 87 | 2.5 | 5 | 5 | 5 | 4 | 5 | 2 | 0 | 0 |
| 88 | 2.5 | 5 | 5 | 5 | 4 | 5 | 2 | 0 | 1 |
| 89 | 2.5 | 5 | 5 | 5 | 4 | 5 | 1 | 0 | 1 |
| 90 | 2.5 | 5 | 5 | 5 | 4 | 5 | 1 | 0 | 1 |
| 92 | 5 | 5 | 5 | 5 | 4 | 5 | 1 | 0 | 1 |
| 94 | 5 | 5 | 5 | 5 | 4 | 5 | 1 | 0 | 1 |
| 95 | 5 | 5 | 5 | 5 | 4 | 5 | 1 | 0 | 1 |
| 96 | 5 | 5 | 5 | 5 | 4 | 5 | 1 | 0 | 1 |

TABLE II-continued

| Comp. No. | Application rate, g/are | Crab-grass | Pig weed | Lamb's quarters | Poly-gonum | Common purs-lane | Maize | Soy-bean | Cotton |
|---|---|---|---|---|---|---|---|---|---|
| 97 | 5 | 5 | 5 | 5 | 4 | 5 | 1 | 0 | 0 |
| 98 | 5 | 4 | 3 | 4 | 2 | 5 | 1 | 0 | 0 |
| 99 | 5 | 2 | 4 | 2 | 2 | 5 | 0 | 0 | 0 |
| 100 | 5 | 4 | 5 | 4 | 3 | 5 | 1 | 0 | 0 |
| 101 | 5 | 3 | 4 | 3 | 3 | 5 | 0 | 0 | 0 |
| 102 | 2.5 | 5 | 5 | 3 | 5 | 5 | 1 | 1 | 0 |
| 103 | 5 | 4 | 5 | 4 | 2 | 5 | 0 | 0 | 0 |
| 104 | 2.5 | 5 | 5 | 5 | 5 | 5 | 1 | 0 | 1 |
| 106 | 10 | 4 | 4 | 4 | 3 | 5 | 1 | 0 | 1 |

EXAMPLE 15

Wagner pots (1/5000 a), each having 200 cm² area, are filled with 3 kg per pot of sand soil and flooded with water, followed by plowing to a paddy field state. On the surface of the soil are sown seeds of barnyard grass *Echinochloa oryzicola* Vasing., umbrella plant *Cyperus difformis* L., monochloria *Monochloria vaginalis* Presl. false pimpernel *Lindernia procumbens* Philcox, toothcup *Rotala* indica Koehne, and a portion of the paddy field soil containing hibernating stems of spike rush *Eleocharis aricularis* Roem. et Shult. is scattered, while, at the same time, seedlings of rice grown separately are transplanted and each pot was filled with water to a depth of 3 cm above the soil surface. The emulsifiable concentrate containing the compound of the general formula (I) is diluted with water to a given concentration of the active ingredient [the compound (I)], and poured in the filled water. 3 weeks after the treatment by application, examination is carried out for the herbicidal effect and injuries. The herbicidal effect and injuries are indicated by the same indication method as employed in Example 14.

TABLE III

| Comp. No. | Application rate, g/are | Rice plant | Barnyard grass | Umbrella plant | Monochoria | False pimpernel | Toothcup | Spike rush |
|---|---|---|---|---|---|---|---|---|
| 1 | 5 | 0 | 1 | 5 | 5 | 5 | 5 | 4 |
|   | 10 | 1 | 4 | 5 | 5 | 5 | 5 | 5 |
| 2 | 5 | 0 | 1 | 5 | 5 | 5 | 5 | 2 |
|   | 10 | 0 | 1 | 5 | 5 | 5 | 5 | 4 |
| 3 | 5 | 0 | 2 | 5 | 5 | 5 | 5 | 3 |
|   | 10 | 1 | 4 | 5 | 5 | 5 | 5 | 5 |
| 4 | 5 | 0 | 1 | 5 | 5 | 5 | 5 | 2 |
|   | 10 | 0 | 2 | 5 | 5 | 5 | 5 | 4 |
| 5 | 5 | 0 | 1 | 5 | 5 | 5 | 5 | 2 |
|   | 10 | 0 | 3 | 5 | 5 | 5 | 5 | 4 |
| 6 | 5 | 0 | 1 | 5 | 5 | 5 | 5 | 3 |
|   | 10 | 1 | 2 | 5 | 5 | 5 | 5 | 4 |
| 7 | 5 | 0 | 1 | 5 | 5 | 4 | 4 | 2 |
|   | 10 | 0 | 4 | 5 | 5 | 5 | 5 | 4 |
| 8 | 5 | 0 | 1 | 5 | 5 | 5 | 5 | 2 |
|   | 10 | 0 | 2 | 5 | 5 | 5 | 5 | 4 |
| 9 | 5 | 0 | 1 | 5 | 5 | 5 | 4 | 4 |
|   | 10 | 0 | 1 | 5 | 5 | 5 | 5 | 5 |
| 13 | 5 | 0 | 1 | 5 | 5 | 5 | 4 | 1 |
|   | 10 | 0 | 1 | 5 | 5 | 5 | 5 | 3 |
| 15 | 5 | 0 | 1 | 5 | 5 | 5 | 5 | 3 |
|   | 10 | 0 | 1 | 5 | 5 | 5 | 5 | 4 |
| 26 | 2.5 | 0 | 3 | 5 | 5 | 5 | 5 | 2 |
|   | 5 | 0 | 4 | 5 | 5 | 5 | 5 | 3 |
| 27 | 5 | 0 | 1 | 5 | 5 | 5 | 5 | 1 |
|   | 10 | 0 | 3 | 5 | 5 | 5 | 5 | 2 |
| 28 | 5 | 0 | 2 | 5 | 5 | 5 | 5 | 3 |
|   | 10 | 0 | 4 | 5 | 5 | 5 | 5 | 4 |
| 30 | 5 | 0 | 3 | 5 | 5 | 5 | 5 | 3 |
|   | 10 | 1 | 5 | 5 | 5 | 5 | 5 | 5 |
| 35 | 5 | 0 | 1 | 5 | 5 | 5 | 5 | 3 |
|   | 10 | 1 | 2 | 5 | 5 | 5 | 5 | 5 |
| 36 | 2.5 | 0 | 1 | 5 | 5 | 4 | 4 | 2 |
|   | 5 | 1 | 1 | 5 | 5 | 5 | 5 | 3 |
| 37 | 2.5 | 0 | 1 | 5 | 5 | 5 | 5 | 3 |
|   | 5 | 0 | 2 | 5 | 5 | 5 | 5 | 4 |
| 38 | 2.5 | 0 | 3 | 5 | 5 | 5 | 5 | 4 |
|   | 5 | 0 | 5 | 5 | 5 | 5 | 5 | 5 |
| 39 | 2.5 | 0 | 3 | 5 | 5 | 5 | 5 | 4 |
|   | 5 | 0 | 4 | 5 | 5 | 5 | 5 | 5 |
| 40 | 2.5 | 0 | 1 | 5 | 5 | 5 | 5 | 2 |
|   | 5 | 0 | 3 | 5 | 5 | 5 | 5 | 3 |
| 42 | 5 | 0 | 1 | 5 | 5 | 5 | 4 | 3 |
|   | 10 | 0 | 2 | 5 | 5 | 5 | 5 | 4 |
| 43 | 5 | 0 | 1 | 5 | 5 | 5 | 5 | 2 |
|   | 10 | 0 | 3 | 5 | 5 | 5 | 5 | 4 |

TABLE III-continued

| Comp. No. | Application rate, g/are | Rice plant | Barnyard grass | Umbrella plant | Monochoria | False pimpernel | Toothcup | Spike rush |
|---|---|---|---|---|---|---|---|---|
| 44 | 5 | 0 | 1 | 5 | 5 | 5 | 5 | 3 |
|  | 10 | 1 | 3 | 5 | 5 | 5 | 5 | 4 |
| 51 | 2.5 | 0 | 3 | 5 | 5 | 5 | 5 | 4 |
|  | 5 | 0 | 4 | 5 | 5 | 5 | 5 | 5 |
| 52 | 2.5 | 0 | 4 | 5 | 5 | 5 | 5 | 4 |
|  | 5 | 1 | 5 | 5 | 5 | 5 | 5 | 5 |
| 55 | 2.5 | 0 | 3 | 5 | 5 | 5 | 5 | 3 |
|  | 5 | 1 | 5 | 5 | 5 | 5 | 5 | 5 |
| 57 | 2.5 | 0 | 3 | 5 | 5 | 5 | 5 | 3 |
|  | 5 | 0 | 5 | 5 | 5 | 5 | 5 | 5 |
| 58 | 2.5 | 0 | 2 | 5 | 5 | 5 | 5 | 2 |
|  | 5 | 0 | 3 | 5 | 5 | 5 | 5 | 4 |
| 60 | 2.5 | 0 | 2 | 5 | 5 | 5 | 5 | 1 |
|  | 5 | 0 | 5 | 5 | 5 | 5 | 5 | 3 |
| 61 | 5 | 0 | 2 | 5 | 5 | 5 | 5 | 3 |
|  | 10 | 0 | 4 | 5 | 5 | 5 | 5 | 3 |
| 62 | 2.5 | 0 | 3 | 5 | 5 | 5 | 5 | 1 |
|  | 5 | 0 | 4 | 5 | 5 | 5 | 5 | 3 |
| 63 | 2.5 | 0 | 5 | 5 | 5 | 5 | 5 | 2 |
|  | 5 | 0 | 5 | 5 | 5 | 5 | 5 | 3 |
| 65 | 2.5 | 0 | 2 | 5 | 5 | 5 | 5 | 2 |
|  | 5 | 0 | 5 | 5 | 5 | 5 | 5 | 3 |
| 66 | 5 | 0 | 3 | 5 | 5 | 5 | 5 | 4 |
|  | 10 | 1 | 5 | 5 | 5 | 5 | 5 | 5 |
| 69 | 2.5 | 0 | 1 | 5 | 5 | 5 | 5 | 1 |
|  | 5 | 1 | 4 | 5 | 5 | 5 | 5 | 4 |
| 70 | 2.5 | 0 | 1 | 5 | 5 | 5 | 5 | 2 |
|  | 5 | 1 | 4 | 5 | 5 | 5 | 5 | 3 |
| 71 | 2.5 | 0 | 1 | 5 | 5 | 4 | 4 | 2 |
|  | 5 | 0 | 1 | 5 | 5 | 5 | 5 | 4 |
| 72 | 2.5 | 0 | 1 | 5 | 4 | 4 | 4 | 1 |
|  | 5 | 0 | 2 | 5 | 5 | 5 | 5 | 3 |
| 74 | 5 | 0 | 1 | 4 | 4 | 4 | 4 | 1 |
|  | 10 | 0 | 2 | 5 | 5 | 5 | 5 | 1 |
| 75 | 2.5 | 1 | 3 | 5 | 5 | 5 | 5 | 3 |
|  | 5 | 1 | 4 | 5 | 5 | 5 | 5 | 4 |
| 76 | 2.5 | 0 | 1 | 5 | 4 | 5 | 5 | 1 |
|  | 5 | 0 | 2 | 5 | 5 | 5 | 5 | 3 |
| 77 | 2.5 | 0 | 1 | 5 | 5 | 5 | 5 | 1 |
|  | 5 | 1 | 3 | 5 | 5 | 5 | 5 | 2 |
| 80 | 2.5 | 0 | 4 | 5 | 5 | 5 | 5 | 2 |
|  | 5 | 1 | 5 | 5 | 5 | 5 | 5 | 4 |
| 82 | 2.5 | 1 | 2 | 5 | 5 | 5 | 5 | 3 |
|  | 5 | 1 | 4 | 5 | 5 | 5 | 5 | 4 |
| 83 | 2.5 | 0 | 2 | 5 | 5 | 5 | 5 | 3 |
|  | 5 | 1 | 4 | 5 | 5 | 5 | 5 | 4 |
| 84 | 2.5 | 0 | 1 | 5 | 5 | 5 | 5 | 3 |
|  | 5 | 1 | 3 | 5 | 5 | 5 | 5 | 4 |
| 85 | 2.5 | 0 | 1 | 5 | 4 | 5 | 5 | 1 |
|  | 5 | 1 | 3 | 5 | 5 | 5 | 5 | 3 |
| 86 | 2.5 | 0 | 1 | 5 | 4 | 5 | 5 | 3 |
|  | 5 | 1 | 3 | 5 | 5 | 5 | 5 | 4 |
| 87 | 2.5 | 0 | 1 | 5 | 5 | 5 | 5 | 2 |
|  | 5 | 1 | 3 | 5 | 5 | 5 | 5 | 4 |
| 88 | 2.5 | 0 | 1 | 5 | 5 | 5 | 5 | 1 |
|  | 5 | 0 | 3 | 5 | 5 | 5 | 5 | 2 |
| 89 | 2.5 | 0 | 1 | 5 | 5 | 5 | 5 | 1 |
|  | 5 | 0 | 3 | 5 | 5 | 5 | 5 | 2 |
| 90 | 2.5 | 0 | 1 | 5 | 5 | 5 | 5 | 1 |
|  | 5 | 0 | 3 | 5 | 5 | 5 | 5 | 3 |
| 97 | 2.5 | 0 | 1 | 5 | 5 | 4 | 4 | 2 |
|  | 5 | 0 | 1 | 5 | 5 | 5 | 5 | 3 |
| 98 | 5 | 0 | 3 | 5 | 5 | 5 | 5 | 3 |
|  | 10 | 1 | 5 | 5 | 5 | 5 | 5 | 4 |
| 99 | 2.5 | 0 | 1 | 5 | 5 | 5 | 5 | 1 |
|  | 5 | 0 | 2 | 5 | 5 | 5 | 5 | 3 |
| 100 | 2.5 | 0 | 3 | 5 | 5 | 5 | 5 | 2 |
|  | 5 | 1 | 4 | 5 | 5 | 5 | 5 | 4 |
| 101 | 5 | 0 | 1 | 5 | 5 | 5 | 5 | 3 |
|  | 10 | 0 | 3 | 5 | 5 | 5 | 5 | 4 |
| 102 | 2.5 | 0 | 2 | 5 | 5 | 5 | 5 | 3 |
|  | 5 | 1 | 4 | 5 | 5 | 5 | 5 | 4 |
| 103 | 2.5 | 0 | 1 | 5 | 5 | 5 | 3 | 1 |
|  | 5 | 1 | 3 | 5 | 5 | 5 | 5 | 3 |
| 104 | 2.5 | 0 | 1 | 5 | 5 | 5 | 5 | 3 |
|  | 5 | 1 | 3 | 5 | 5 | 5 | 5 | 4 |

What is claimed is:

1. A tetrahydrophthalamide compound of the formula:

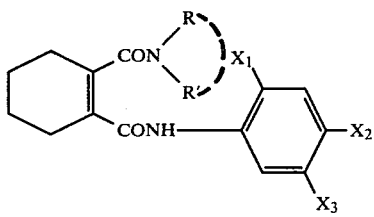

wherein
- $X_1$ is hydrogen or halogen;
- $X_2$ is halogen, $C_{1-3}$ alkoxy or halogen-substituted benzyloxy;
- at least one of $X_1$ and $X_2$ is halogen;
- $X_3$ is hydrogen, $C_{1-3}$ alkoxy or alkenyloxy; R and R' are the same or different
  - (a) alkyl,
  - (b) cycloalkyl,
  - (c) alkenyl, or
  - (d) phenyl, each of which may be substituted: or R and R' may jointly, together with the nitrogen atom adjacent to R and R', form an aliphatic heterocyclic ring containing one or two nitrogens, or nitrogen and oxygen.

2. A compound according to claim 1, wherein R and R' are alkyl.

3. A compound according to claim 2, wherein the alkyl is methyl, ethyl, propyl, isopropyl, butyl, isobutyl, sec-butyl, t-butyl, pentyl, isopentyl, hexyl, heptyl, octyl, nonyl, decyl, lauryl or stearyl.

4. A compound according to claim 2, wherein the alkyl is $C_{1-10}$ alkyl.

5. A compound according to claim 1, wherein R and R' are cycloalkyl.

6. A compound according to claim 1 wherein R and R' are alkenyl.

7. A compound according to claim 1, wherein R and R' form, jointly together with the nitrogen atom adjacent to R and R', an aliphatic heterocyclic ring containing one or two nitrogens, or nitrogen and oxygen.

8. A compound according to claim 2, wherein the alkyl is of 1 to 4 carbon atoms.

9. A compound according to claim 1, wherein the substituent on the alkyl is hydroxyl, cyano, halogen, alkoxy of 1 to 3 carbon atoms or phenyl.

10. A compound according to claim 5, wherein the cycloalkyl is cyclohexyl.

11. A compound according to claim 6, wherein the alkenyl is allyl.

12. A compound according to claim 1, wherein the substituent on the phenyl is alkyl of 1 to 4 carbon atoms or alkoxy of 1 to 4 carbon atoms.

13. A compound according to claim 1 or 7, wherein the aliphatic heterocyclic ring which is jointly formed with R and R' is a member selected from the group consisting of aziridino, azetidino, piperidino, pyrrolidino, hexahydroazepino, piperazino, N-methylpiperazino, morpholino, 2,6-dimethylmorpholino, 2-pyrrolino, 3-pyrrolino, 2-pipecolino and 3-pipecolino.

14. A compound according to claim 1, wherein $X_1$ is hydrogen, $X_2$ is halogen and $X_3$ is hydrogen.

15. A compound according to claim 1, wherein $X_1$ is hydrogen, $X_2$ is chlorine or bromine and $X_3$ is alkoxy of 1 to 3 carbon atoms or allyloxy.

16. A compound according to claim 1, wherein $X_1$ is chlorine, $X_2$ is chlorine and $X_3$ is alkoxy of 1 to 3 carbon atoms or allyloxy.

17. A compound according to claim 1, wherein $X_1$ is fluorine, $X_2$ is chlorine or bromine and $X_3$ is hydrogen.

18. A compound according to claim 1, wherein $X_1$ is fluorine, $X_2$ is chlorine, $X_3$ is hydrogen, and either one of R and R' is methyl or ethyl and the other is a member selected from the group consisting of n-butyl, benzyl, phenyl which may be optionally substituted by methyl or methoxy, or R and R' may form, together with nitrogen adjacent to R and R', a member selected from the group consisting of piperidino, pyrrolidino, morpholino, 2,6-dimethylmorpholino, N-methylpiperazino and hexahydroazepino.

19. The compound according to claim 1, which is N-methyl-N-n-butyl-N'-(2-fluoro-4-chlorophenyl)-3,4,5,6-tetrahydrophthalamide.

20. The compound according to claim 1, which is N,N-tetramethylene-N'-(2-fluoro-4-chlorophenyl)-3,4,5,6-tetrahydrophthalamide.

21. The compound according to claim 1, which is N,N-diethyleneoxy-N'-(2-fluoro-4-chlorophenyl)-3,4,5,6-tetrahydrophthalamide.

22. A herbicidal composition which contains as an active ingredient, an effective amount of a tetrahydrophthalamide compound of the formula:

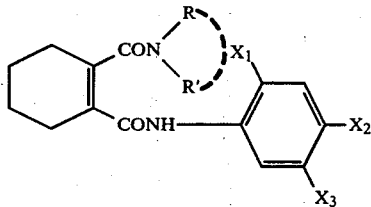

wherein $X_1$ is hydrogen or halogen; $X_2$ is halogen, $C_{1-3}$ alkoxy or halogen-substituted benzyloxy; $X_3$ is hydrogen, $C_{1-3}$ alkoxy or alkenyloxy; R and R' are the same or different alkyl, cycloalkyl, alkenyl or phenyl, each of which may be substituted, or R and R' may jointly, together with the nitrogen atom adjacent to R' and R, form an aliphatic heterocyclic ring containing one or two nitrogens, or nitrogen and oxygen, and a suitable carrier therefor.

23. A method of killing weeds comprising administering the composition of claim 22 to a field in an amount sufficient to provide between about 1 to 50 g of the tetrahydrophthalamide compound per are.

* * * * *